United States Patent
Ou et al.

(10) Patent No.: US 6,459,006 B1
(45) Date of Patent: Oct. 1, 2002

(54) SELECTIVE METHYLATION TO PARA-XYLENE USING FUEL SYNGAS

(75) Inventors: John D. Y. Ou, Houston, TX (US); Thomas J. Waddick, League City, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 09/433,387

(22) Filed: Nov. 3, 1999

Related U.S. Application Data (63) Continuation-in-part of application No. 09/312,104, filed on May 14, 1999, now Pat. No. 6,388,159.

(51) Int. Cl.[7] ............................................. C07C 15/107
(52) U.S. Cl. ........................ 585/454; 585/467; 585/469
(58) Field of Search ................................. 585/454, 446, 585/467, 469

(56) References Cited

U.S. PATENT DOCUMENTS

| | | | |
|---|---|---|---|
| 3,965,207 A | 6/1976 | Weinstein | 260/671 M |
| 4,086,289 A | 4/1978 | Seitzer | 260/671 |
| 4,274,982 A | 6/1981 | Chu | 252/455 Z |
| 4,357,264 A | 11/1982 | Chu | 252/455 Z |
| 4,358,362 A * | 11/1982 | Smith et al. | 208/91 |
| 4,377,718 A | 3/1983 | Sato et al. | 585/467 |
| 4,409,412 A | 10/1983 | Haag et al. | 585/454 |
| 4,465,238 A | 8/1984 | Patel et al. | 239/590.3 |
| 4,486,616 A | 12/1984 | Chu et al. | 585/456 |
| 4,487,983 A | 12/1984 | Miller et al. | 585/454 |
| 4,487,984 A | 12/1984 | Imai | 585/454 |
| 4,507,400 A | 3/1985 | Miller et al. | 502/63 |
| 4,665,238 A | 5/1987 | Imai et al. | 468/794 |
| 4,670,616 A | 6/1987 | Simone et al. | 585/467 |
| 5,034,362 A | 7/1991 | Chu et al. | 502/60 |
| 5,476,823 A | 12/1995 | Beck et al. | 502/60 |
| 5,625,104 A | 4/1997 | Beck et al. | 585/475 |
| 5,675,047 A | 10/1997 | Beck et al. | 585/467 |
| 5,689,027 A | 11/1997 | Aichandani et al. | 585/481 |
| 5,849,968 A | 12/1998 | Beck et al. | 585/481 |

FOREIGN PATENT DOCUMENTS

| | | | |
|---|---|---|---|
| EP | 0 057 514 | 8/1982 | ............. C07C/2/86 |
| WO | WO 94/27934 | 12/1994 | |
| WO | WO 97/45387 | 12/1997 | |
| WO | WO 98/16469 | 4/1998 | |

OTHER PUBLICATIONS

Methylation of Toluene with Synthesis Gas on Zn–Cr Oxide/ZSM–5 Zeolite Composite Catalysts, Nippon Kagaku Kaishi, Journal of the Chemical Society of Japan, No. 3, pp 595–597, 1989.

Mysov et al., "The investigation of processes of the organic products synthesis from natural gas via syngas," Natural Gas Conversion V. Studies in Surface Science and Catalysis, vol. 119, pp 533–538, 1998.

* cited by examiner

*Primary Examiner*—Thuan D. Dang (57) ABSTRACT

It has been discovered that para-xylene (PX) can be synthesized with improved selectivity by reacting an aromatic compound such as toluene and/or benzene with a reactant(s) from fuel syngas such as a combination of hydrogen and carbon monoxide and/or carbon dioxide and/or methanol, or methylating agents produced therefrom. The combination of the selective methylation technology and a source of fuel syngas creates several advantages including simplification of the selective methylation process and utilization of low cost feeds. The fuel syngas is used on a once-through basis.

26 Claims, 1 Drawing Sheet

SELECTIVE METHYLATION TO PARA-XYLENE USING FUEL SYNGAS

CROSS-REFERENCE TO RELATED PATENT APPLICATION

This patent application is a Continuation-in-Part application from U.S. patent application Ser. No. 09/312,104, filed on May 14, 1999 now U.S. Pat. No. 6,388,159.

FIELD OF THE INVENTION

The present invention relates to methods for synthesis of xylenes by catalytic methylation of toluene and benzene, and more particularly relates, in one embodiment, to methods for direct, selective synthesis of para-xylene by catalytic methylation of toluene and benzene using fuel syngas.

BACKGROUND OF THE INVENTION

Of the xylene isomers, i.e., ortho-, meta-, and para-xylene, the para-xylene (PX) is of particular value as a large volume chemical intermediate in a number of applications being useful in the manufacture of terephthalates which are intermediates for the manufacture of PET. One source of feedstocks for manufacturing PX is by disproportionation of toluene into xylenes. One of the disadvantages of this process is that large quantities of benzene are also produced. Another source of feedstocks used to obtain PX involves the isomerization of a feedstream that contains non-equilibrium quantities of mixed ortho- and meta-xylene isomers (OX and MX, respectively) and is lean with respect to PX content. A disadvantage of this process is that the separation of the PX from the other isomers is expensive.

Zeolites are known to catalyze the reaction of toluene with other reactants to make xylenes. Some zeolites are silicate-based materials which are comprised of a silica lattice and, optionally, alumina combined with exchangeable cations such as alkali or alkaline earth metal ions. Although the term "zeolites" includes materials containing silica and optionally alumina, it is recognized that the silica and alumina portions may be replaced in whole or in part with other oxides. For example, germanium oxide, tin oxide, phosphorus oxide, and mixtures thereof can replace the silica portion. Boron oxide, iron oxide, gallium oxide, indium oxide, and mixtures thereof can replace the alumina portion. Accordingly, the terms "zeolite", "zeolites" and "zeolite materials", as used herein, shall mean not only materials containing silicon and, optionally, aluminum atoms in the crystalline lattice structure thereof, but also materials which contain suitable replacement atoms for such silicon and aluminum, such as gallosilicates, borosilicates, ferrosilicates, and the like.

The term "zeolite, "zeolites", and "zeolite materials" as used herein, besides encompassing the materials discussed above, shall also include aluminophosphate-based materials. Aluminophosphate zeolites are made of alternating $AlO_4$ and $PO_4$ tetrahedra. Aluminophosphate-based materials have lower acidity compared to aluminosilicates. The lower acidity eliminates many side reactions, raises reactants' utilization, and extends catalyst life. Aluminophosphate-based zeolites are often abbreviated as ALPO. Substitution of silicon for P and/or a P-Al pair produces silicoaluminophosphate zeolites, abbreviated as SAPO.

Processes have been proposed for the production of xylenes by the methylation of toluene using a zeolite catalyst. For instance, U.S. Pat. No. 3,965,207 involves the methylation of toluene with methanol using a zeolite catalyst such as a ZSM-5. U.S. Pat. No. 4,670,616 involves the production of xylenes by the methylation of toluene with methanol using a borosilicate zeolite which is bound by a binder such as alumina, silica, or alumina-silica. One of the disadvantages of such processes is that catalysts deactivate rapidly due to build up of coke and heavy by-products. Another disadvantage is that methanol selectivity to para-xylene, the desirable product, has been low, in the range of 50 to 60%. The balance is wasted on the production of coke and other undesirable compounds.

It has been further demonstrated that alkylaromatic compounds can be synthesized by reacting an aromatic compound such as toluene with a mixture of carbon monoxide (CO), carbon dioxide ($CO_2$), and hydrogen ($H_2$) (synthesis gas) at alkylation conditions in the presence of a catalyst system, which comprises (1) a composite of oxides of zinc, copper, chromium, and/or cadmium; and (2) an aluminosilicate material, either crystalline or amorphous, such as zeolites or clays; as disclosed in U.S. Pat. Nos. 4,487,984 and 4,665,238. Such catalyst systems, however, are not capable of producing greater than equilibrium concentrations of para-xylene (PX) in the xylene-fraction product. Typically, the xylene-fraction product contains a mixture of xylene isomers at or near the equilibrium concentration, i.e., 24% PX, 54% MX, and 22% OX. The lack of para-xylene selectivity in alkylation of toluene with syngas can be caused by (1) the acidic sites on the surface outside the zeolite channels, and/or (2) the channel structure not being able to differentiate para-xylene from its isomers. It would be desirable for the toluene alkylation to be more para-alkyl selective due to the much higher value of PX compared to that of MX and OX. Furthermore, such processes suffer from catalyst deactivation as well. In addition, the prior art disclosed neither syngas alkylation to alkyl aromatic compounds nor syngas selective alkylation to high purity PX using alumino-phosphate-based materials.

It has been recognized that certain zeolites can be modified to enhance their molecular-sieving or shape-selective capability. Such modification treatments are usually called "zeolite selectivation." Selectivated zeolites can more accurately differentiate molecules on the basis of molecular dimension or steric characteristics than the unselectivated precursors. For example, silanized ZSM-5 zeolites adsorbed PX much more preferentially over MX than untreated ZSM-5. It is believed that the deposition of silicon oxide onto zeolite surfaces from the silanization treatment has (1) passivated the active sites on the external surface of zeolite crystals, and (2) narrowed zeolitic pores to facilitate the passage of the smaller PX molecules and prevent the bigger MX and OX molecules from entering or exiting from the pores. In this application, the term "para-alkyl selectivation" refers to modifying a catalyst or catalytic reaction system so that it preferentially forms more PX than the expected equilibrium proportions relative to the other isomers.

Zeolite selectivation can be accomplished using many techniques. Reports of using compounds of silicon, phosphorous, boron, antimony, coke and other carbon compounds, magnesium, etc. for selectivation have been documented. Unfortunately many, if not most of the zeolites used in the prior art have undesirably short active lifetimes before they deactivate and have to be reactivated or replaced.

There remains a need for still further improved processes for catalytic PX synthesis which minimizes or avoids the disadvantages of prior systems, which include low PX selectivity, rapid catalyst deactivation, and the like. Further, it would be desirable if a method for selective methylation to PX could be devised which employed a low cost source of methylating agent, such as fuel syngas.

SUMMARY OF THE INVENTION

Accordingly, it is an object of the present invention to provide a method in which PX of high product concentration is synthesized via alkylation of toluene and/or benzene with fuel syngas in a catalytic reaction system.

It is another object of the present invention to provide a method for producing PX in greater than equilibrium product concentration, e.g. greater than 30%, in the xylene product fraction as compared to prior, equilibrium concentrations of about 24%.

Still another object of the invention is to provide a method for the direct, selective production of PX from toluene and/or benzene which has a high aromatic conversion, e.g. at least above 5%, preferably above 15%, most preferably as high as possible.

In carrying out these and other objects of the invention, there is provided, in one form, a method for forming para-xylene (PX) from fuel syngas involving, optionally desulfurizing the fuel syngas, reacting the fuel syngas on a once-through basis with a feed containing an aromatic compound of toluene, benzene and mixtures thereof, in the presence of a catalytic reaction system which converts at least 5% of the aromatic compound to a mixture of xylenes, where PX comprises at least 30% of the mixture of xylenes. A methylating agent formed from the fuel syngas reacts with the PX.

It should be stressed that the invention provides a process for increased selectivity to para-xylene. Further, the invention employs aluminophosphate-based catalysts for selective para-xylene synthesis, whether or not the aluminophosphate-based materials are para-alkyl selectivated. Additionally, the invention prolongs catalyst lifetime by reducing, even eliminating catalyst deactivation, as compared with prior PX forming processes. Another advantage of the invention is the simultaneous cracking of paraffins and olefins present while processing unextracted toluene, or unextracted mixtures of toluene and benzene, as well as reacting fuel syngas on a once-through basis.

DETAILED DESCRIPTION OF THE INVENTION

Figure 1:
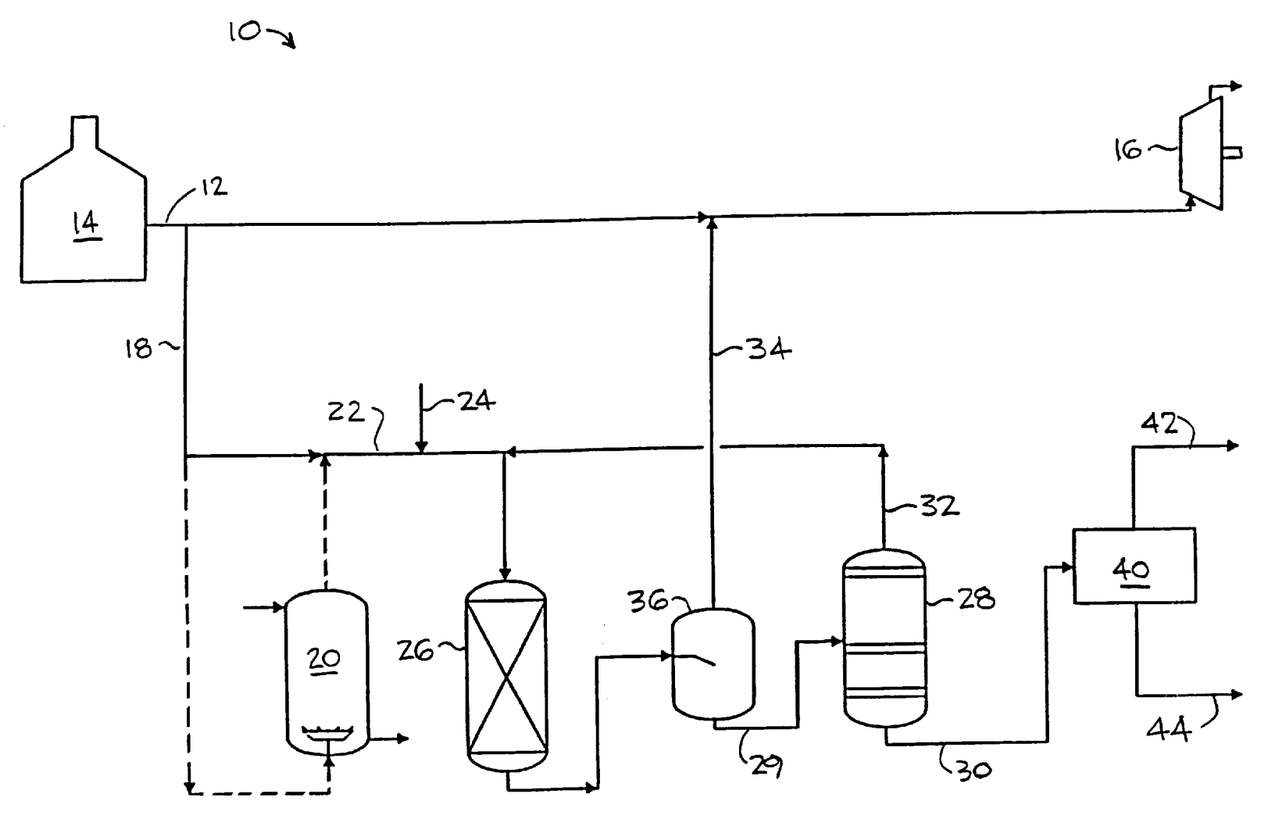
The FIGURE shows a schematic diagram of one embodiment of a process arrangement for forming PX from fuel syngas according to the method of the invention.

The present invention relates to a process to synthesize PX with para-alkyl selective alkylation of toluene and/or benzene with a mixture containing, as predominant components thereof, hydrogen, carbon monoxide, and/or carbon dioxide and/or methanol in the presence of a catalyst system. A method has been discovered by which the product selectivity to para-xylene for an aromatic alkylation process using as alkylating agents mixtures of $H_2$, CO, and/or $CO_2$ and/or methanol from fuel syngas is significantly enhanced. The process of the invention using fuel syngas has advantages including, but not limited to:

1) enabling the use of low-cost fuel syngas;
2) eliminating the need for-recycling unreacted syngas and associated equipment;
3) eliminating the need for a significant purge stream of unreacted syngas;
4) enabling the use of the relatively low-cost unextracted toluenelbenzene or straight reformate heart cut, and
5) eliminating the need for a significant purge stream of unreacted toluene, benzene and/or reformate.

Details of the implementation of the fuel syngas use in the selective methylation process will be discussed below.

The improvement in para-xylene selectivity is achieved by treating the molecular sieve zeolite materials with proper chemical compounds to (1) inhibit the external acidic sites to minimize aromatic alkylation on the non-para positions, and/or the isomerization of the para-alkylated compounds, and/or (2) impose more restrictions on the channel structure to facilitate the formation and transport of para-alkylated aromatic compounds, in one non-limiting explanation of the mechanism of the invention. It must be understood that such treatment may be performed on aluminophosphate catalyst reaction systems of this invention, but that some aluminophosphate: catalyst reaction systems do not require this para-alkyl selectivation treatment to be effective at para-alkyl selectivation in the methods of this invention.

The catalytic reaction systems suitable for this invention include (1) a first component of one or more than one of the metals or oxides of the metal elements selected: from Groups 1, 2, 3, 4, 5, 6, 7, 8, 9, 10, 11, 12, 13, 14, 15 and 16 (new IUPAC notation, e.g. zinc, copper, chromium, cadmium, palladium, ruthenium, manganese, etc.), and (2) a second component of one or more than one of the zeolite or amorphous materials, some of which are selectivated for para-position selectivity. The first and second components may be chemically mixed, physically mixed, and combinations thereof, as will be described.

One type of the zeolite materials would be silicate-based zeolites such as faujasites, mordenites, pentasils, etc.

Zeolite materials suitable for this invention include silicate-based zeolites and amorphous compounds. Silicate-based zeolites are made of alternating $SiO_2$ and $MO_x$ tetrahedra, where in the formula M is an element selected from the Groups 1 through 16 of the Periodic Table (new IUPAC). These types of zeolites have 8-, 10-, or 12-membered oxygen ring channels. Silicate-based materials are generally acidic. The more preferred zeolites of this invention include 10- and 12-membered ring zeolites, such as ZSM-5, ZSM-11, ZSM-22, ZSM48, ZSM-57, etc.

One of the disadvantages to the use of many unselectivated silicate-based materials for such PX synthesis systems is the lack of product selectivity (i.e. an undesirably broad product distribution results). The acidity and structure of many silicate-based materials are such that they often promote many undesirable side reactions (e.g. dealkylation, isomerization, multi-alkylation, oligomerization, and condensation) which deactivate the catalysts and lower the product value. It follows that, silicate-based materials are typically not capable of delivering the shape selectivity for increasing the yield for high-value products such as para-xylene (PX).

Some of the silicate-based materials have one-dimensional channel structures, which are capable of generating higher-than-equilibrium PX selectivity. These materials may optionally be para-alkyl selectivated. Other silicate-based materials having two- or three-dimensional channel structures are preferably para-alkyl selectivated or modified to be more selective through the use of certain chemical compounds, as will be described, such as organometallic compounds and compounds of elements selected from Groups 1–16. In one embodiment, the selectivation of the zeolite materials including the silicate-based materials can be accomplished using compounds including, but not necessarily limited to silicon, phosphorus, boron, antimony, magnesium compounds, coke, and the like, and mixtures thereof.

Other silicate-based materials suitable for the second component include zeolite bound zeolites as described in WO 97/45387, incorporated herein by reference. Zeolite bound zeolite catalysts useful in the present invention concern first crystals of an acidic intermediate pore size first zeolite and a binder comprising second crystals of a second zeolite. Unlike zeolites bound with amorphous material such as silica or alumina to enhance the mechanical strength of the zeolite, the zeolite bound zeolite catalyst suitable for use in the present process does not contain significant amounts of non-zeolitic binders.

The first zeolite used in the zeolite bound zeolite catalyst is an intermediate pore size zeolite. Intermediate pore size zeolites have a pore size from about 5 to about 7 Å and include, for example, AEL, MFI, MEL, MFS, MEI, MTW, EUO, MTT, HEU, FER, and TON structure type zeolites. These zeolites are described in *Atlas of Zeolite Structure Types*, eds. W. H. Meier and D. H. Olson, Butterworth-Heineman, Third Edition, 1992, which is hereby incorporated by reference. Examples of specific intermediate pore size zeolites include, but are not limited to, ZSM-5, ZSM-11, ZSM-12, ZSM-22, ZSM-23, ZSM-34, ZSM-35, ZSM-38, ZSM48, ZSM-50, and ZSM-57. Preferred first zeolites are galliumsilicate zeolites having an MFI structure and aluminosilicate zeolites having an MFI structure.

The second zeolite will usually have an intermediate pore size and have less activity than the first zeolite. Preferably, the second zeolite will be substantially non-acidic and will have the same structure type as the first zeolite. The preferred second zeolites are aluminosilicate zeolites having a silica to alumina mole ratio greater than 100 such as low acidity ZSM-5. If the second zeolite is an aluminosilicate zeolite, the second zeolite will generally have a silica to alumina mole ratio greater than 200:1, e.g., 500:1; 1,000:1, etc., and in some applications will contain no more than trace amounts of alumina. The second zeolite can also be silicalite, i.e., a MFI type substantially free of alumina, or silicalite 2, a MEL type substantially free of alumina. The second zeolite is usually present in the zeolite bound zeolite catalyst in an amount in the range of from about 10% to 60% by weight based on the weight of the first zeolite and, more preferably, from about 20% to about 50% by weight.

The second zeolite crystals preferably have a smaller size than the first zeolite crystals and more preferably will have an average particle size from about 0.1 to about 0.5 microns. The second zeolite crystals, in addition to binding the first zeolite particles and maximizing the performance of the catalyst will preferably intergrow and form an over-growth which coats or partially coats the first zeolite crystals. Preferably, the crystals will be resistant to attrition.

The zeolite bound zeolite catalyst suitable for the process of the present invention is preferably prepared by a three step procedure. The first step involves the synthesis of the first zeolite crystals prior to converting it to the zeolite bound zeolite catalyst. Next, a silica-bound aluminosilicate zeolite can be prepared preferably by mixing a mixture comprising the aluminosilicate crystals, a silica gel or sol, water and optionally an extrusion aid and, optionally, the metal component until a homogeneous composition in the form of an extrudable paste develops. The final step is the conversion of the silica present in the silica-bound catalyst to a second zeolite which serves to bind the first zeolite crystals together.

As noted, aluminophosphate-based materials may be used in conjunction with metal oxides for aromatic alkylation with syngas. Aluminophosphate-based materials usually have lower acidity compared to silicate-based materials. The lower acidity eliminates many side reactions, raises reactants' utilization, and extends catalyst life. In addition, some of the medium-pore aluminophosphate-based materials have unique channel structures that could generate the desirable shape selectivity.

Further, catalytic reaction systems suitable for this invention include aluminophosphate-based materials and amorphous compounds. Aluminophosphate-based materials are made of alternating $AlO_4$ and $PO_4$ tetrahedra. Members of this family have 8- (e.g. $AlPO_4$-12, -17, -21, -25, -34, -42, etc.), 10- (e.g. $AlPO_4$-11, 41, etc.), or 12- ($AlPO_4$-5, -31, etc.) membered oxygen ring channels. Although $AlPO_4$s are neutral, substitution of Al and/or P by cations with lower charge introduces a negative charge in the framework, which is countered by cations imparting acidity.

By turn, substitution of silicon for P and/or a P-Al pair turns the neutral binary composition (i.e. Al, P) into a series of acidic-ternary-composition (Si, Al, P) based SAPO materials, such as SAPO-5, -11, -14, -17, -18, -20, -31, -34, -41, -46, etc. Acidic ternary compositions can also be created by substituting divalent metal ions for aluminum, generating the MeAPO materials. Me is a metal ion which can be selected from the group consisting of, but not limited to, Mg, Co, Fe, Zn and the like. Acidic materials such as MgAPO (magnesium substituted), CoAPO (cobalt substituted), FeAPO (iron substituted), MnAPO (manganese substituted), ZnAPO (zinc substituted) etc. belong to this category. Substitution can also create acidic quaternary-composition based materials such as the MeAPSO series, including FeAPSO (Fe, Al, P, and Si), MgAPSO (Mg, Al, P, Si), MnAPSO, CoAPSO, ZnAPSO (Zn, Al, P, Si), etc. Other substituted aluminophosphate-based materials include EIAPO and EIAPSO (where EI=B, As, Be, Ga, Ge, Li, Ti, etc.) As mentioned above, these materials have the appropriate acidic strength for syngas/aromatic alkylation. The more preferred aluminophosphate-based materials of this invention include 10- and 12-membered ring materials (SAPO-11, -31, -41; MeAPO-11, -31, -41; MeAPSO-11, -31, -41; EIAPO-11, -31, 41; EIAPSO-11, -31, -41, etc.) which have significant shape selectivity due to their narrow channel structure.

It has been discovered that it may not be necessary for the alumino-phosphate-based materials to be processed in a para-alkyl selectivation step for good selectivity when producing para-xylene. Optionally, however, these aluminophosphates may be para-alkyl selectivated or modified to be more selective through the use of certain chemical compounds, as will be described, such as organometallic compounds and compounds of elements selected from Groups 1–16. In one embodiment, the para-alkyl selectivation of the zeo-lite materials including the aluminophosphate-based materials can be accomplished using compounds including, but not necessarily limited to silicon, phosphorus, boron, antimony, magnesium compounds, coke, and the like, and mixtures thereof.

The composition of the proposed catalytic reaction systems may be from 5 wt. % metals or metal oxides first component/95 wt. % silicate-based material or aluminophosphate-based material second component, to 95 wt. % metals or metal oxides first component/5 wt. % silicate-based material or aluminophosphate-based material second component. The preparation of the catalytic reaction systems can be accomplished with several techniques known to those skilled in the art. Some examples are given below.

Para-alkyl selectivation involves the treatment of the above mentioned catalytic reaction system materials with proper chemical compounds. Some para-alkyl selectivation treatments are known, e.g. using silicon compounds. Other compounds that may be used include, but are not limited to compounds of phosphorus, boron, antimony, magnesium, and the like, and coke, and the like. Para-alkyl selectivation treatments of the materials of the above catalytic reaction systems, such as by using the metals/metal oxides first component to selectivate, can be carried out either prior to the selective formation of PX (ex situ) or during the PX formation (in situ). In the in situ embodiment, the selectivating agents are added with the feed or the feed itself could be used as the selectivating agent to the reactor containing a catalytic reaction system.

In more detail, in one non-limiting embodiment, the technique for selectivating the materials useful in the method of this invention is based on the consideration that by depositing on a silicate-based material or aluminophosphate-based material one or more than one of the organometallic compounds which are too bulky to enter the channels (or other para-alkyl selectivating agents), one should be able to modify only the external surface and regions around channel mouth. The fact that the para-alkyl selectivation agent does not enter the channels preserves the active sites inside the channels. Since the channel active sites account for the majority of the total active sites, their remaining active prevents any significant loss of reactivity or conversion.

It will be understood that the para-alkyl selectivation techniques of this invention may be practiced before or after the silicate-based materials or aluminophosphate-based materials are mixed with or combined chemically or physically with metals or metal oxides. That is, in some embodiments, the silicate-based materials and aluminophosphate-based materials may be para-alkyl selectivated before combination with metals or metal oxides. In other embodiments, silicate-based materials and aluminophosphate-based materials may be para-alkyl selectivated after combination with metals or metal oxides. The former process might be termed "pre-selectivation", while the latter process may be termed "post-selectivation".

One type of the bulky organometallic compounds suitable for para-alkyl selectivating 10-member-ring zeolites, such as the ZSM family (e.g. ZSM-5, -11, -22, -48, etc.), mordenite, etc., is the salts of large organic anions and metallic cations. The organic anions can be selected from molecules containing carboxylic and/or phenolic functional groups, including but not limited to phthalate, ethylenediaminetetraacetic acid (EDTA), vitamin B-5, trihydroxy benzoic acid, pyrogallate, salicylate, sulfosalicylate, citrate, naphthalene dicarboxylate, anthradiolate, camphorate, and others. The metallic cations can be selected from the element(s) of Groups 1, 2, 3, 4, 5, 6, 7, 8, 9, 10, 11, 12, 13, 14, 15, and 16 (new IUPAC notation). Other compounds for para-alkyl selectivating the silicate-based and aluminophosphate-based materials include, but are not necessarily limited to silicon, phosphorus, boron, antimony, magnesium compounds, coke, and the like, and mixtures thereof.

Para-alkyl selectivation of silicate-based materials and aluminophosphate-based materials with the above mentioned organometallic salts can be accomplished by various means. For example, one can use impregnation of a solution of an organometallic salt onto a silicate-based material or aluminophosphate-based materials. Either water or any suitable organic solvent can be used. Addition of non-metallic salts and/or adjustments of pH to facilitate the treatment are optional. Heat will be provided to drive off the solvent leaving behind a material coated homogeneously with the organometallic salt. Drying and calcination of the coated zeolite or aluminophosphate-based materials at appropriate temperatures will turn the salt into metal oxide. Alternatively, one can use a dry-mix technique, which involves mixing directly a zeolite in the form of powder or particles with a organometallic salt also in the form of powder or particles without the use of any solvent. The mixture will then be subjected to heat treatment, which facilitates the dispersion of the salt over the material and eventually turn the salt into metal oxide.

Known techniques for ex situ and in situ catalytic reaction system modification can be incorporated into producing the para-alkyl selectivated catalytic reaction systems of the present invention in accordance herewith, such as those seen in U.S. Pat. Nos. 5,476,823 and 5,675,047, incorporated herein by reference.

In one embodiment, the same metals and/or metal oxide components used in the catalytic reaction system can be used alone or together to selectivate the silicate-based material or aluminophosphate-based material components.

The catalytic reaction systems can be prepared by adding solutions of metal salts either in series to or as a mixture with the fine powder or particles such as extrudates, spheres, etc. of the unselectivated silicate-based materials having one dimensional channel structures, or optionally ex situ para-alkyl selectivated silicate-based materials, unselectivated aluminophosphate-based materials, or optionally ex situ para-alkyl selectivated aluminophosphate-based materials, until incipient wetness is reached. The solvent (water or other solvents) can be evacuated under heat or vacuum using a typical equipment such as a rotary evaporator. The final product is dried, calcined, and pelletized, if necessary.

Alternatively, solutions of metal salts and the ex situ para-alkyl selectivated fine powder or particles such as extrudates, spheres, etc. of the silicate-based and aluminophosphate-based materials are thoroughly mixed. A dilute basic solution (e.g. ammonia, sodium carbonate, potassium hydroxide, etc.) is used to adjust the pH value of the mixture to facilitate the precipitation of metal hydroxides and zeolites. The precipitate is filtered and washed thoroughly with water. The final product is dried, calcined, and pelletized, if necessary.

The catalytic reaction systems can also be prepared using physical mixing. Finely divided powders of metal(s) or metal oxide(s), or powders of metal(s) or metal oxide(s) supported on any inert materials, are mixed thoroughly with finely divided powder of the ex situ para-alkyl selectivated silicate-based materials, unselectivated aluminophosphate-based materials, or optionally ex situ para-alkyl selectivated aluminophosphate-based materials in a blending machine or a grinding mortar. The mixture is optionally pelletized before use.

If the catalytic reaction system is mixed with a binder, such as silica gel or sol or the like, an extrudable paste may be formed. The resulting paste can be molded, e.g. extruded, and cut into small strands which can then be dried and calcined.

The catalytic reaction system can also be prepared by mixing physically the particles of silicate-based material or aluminophosphate-based materials components and the particles of the metal and/or metal oxide first components. The same metals and/or metal oxides can also be used alone or together to selectivate catalytic reaction systems and thus simultaneously catalyze syngas reactions.

The catalytic reaction system can also be formed by packing the first and the second components in a stacked-bed manner with some of the first component in front of the physical or chemical mixture of the first and second components.

Prior to exposing the catalytic reaction systems to the feed components of toluene and/or benzene, and fuel syngas the catalytic reaction systems can optionally be activated under a reducing environment (e.g. 1–80% $H_2$ in $N_2$) at 150–500° C., and 1–200 atm ($1.01 \times 10^5$–$2.03 \times 10^7$ Pa) for 2–48 hours.

The average crystal size of the crystals in the silicate-based material or aluminophosphate-based materials, is preferably from above 0.1 micron to about 100 microns, more preferably from about 1 micron to about 100 microns.

Procedures to determine crystal size are known to persons skilled in the art. For instance, crystal size may be determined directly by taking a suitable scanning electron microscope (SEM) picture of a representative sample of the crystals.

The methylation process can be carried out as a batch type, semi-continuous or continuous operation utilizing a fixed, moving bed, or CSTR catalytic reaction system, with or without recycle. Multiple injection of the fuel syngas may be employed. The methylating agent includes CO, $CO_2$ and $H_2$ and/or $CH_3OH$ and derivatives thereof. The methylating agent may be the CO, $CO_2$ and $H_2$ of the fuel syngas directly, or if a catalytic reaction system suitable for forming other methylating agents such as $CH_3OH$ and/or other agents is employed, these agents and derivatives thereof may be used as well. The methylating agent reacts with benzene to form toluene. Toluene reacts with the methylating agent to form a xylene, preferably PX in this invention.

Toluene and/or benzene and the methylating agent(s) are usually premixed and fed together into the reaction vessel to maintain the desired ratio between them with no local concentration of either reactant to disrupt reaction kinetics. Individual feeds can be employed, however, if care is taken to insure good mixing of the reactant vapors in the reaction vessel. Optionally, instantaneous concentration of fuel syngas can be kept low by staged additions thereof. By staged additions, the ratios of toluene and/or benzene to syngas concentrations can be maintained at optimum levels to give good aromatic compound conversions and better catalytic reaction system stability. Hydrogen gas can also serve as an anticoking agent and diluent.

The method of this invention, particularly when using para-alkyl selectivated catalytic reaction systems, stabilizes catalytic reaction system performance and increases catalytic reaction system life. That is, catalytic reaction system deactivation is slowed and even prevented. With properly para-alkyl selectivated catalytic reaction systems, it is expected that the catalytic reaction system may not have to be regenerated at all. This is in part due to the silicate-based materials and aluminophosphate-based materials being para-alkyl selectivated. With production selective to PX, less by-products, such as heavy aromatics, are formed which would deactivate the catalytic reaction systems. This characteristic is not shown or taught by the prior art.

Further, in one non-limiting embodiment of the invention, there is a belief that the catalytic reaction systems of this invention have the capability of preventing or reducing the side reactions of the methylating agents with themselves, and in particular that the para-alkyl selectivated catalytic reaction systems function to catalyze more than one reaction, that is, that a syngas reaction is catalyzed to form methylating agents which react with benzene and/or toluene to produce PX. However, because the methylating agent is produced on a local, molecular scale, its concentrations are very low (as contrasted with feeding a methylating agent as a co-reactant). It has been demonstrated that feeding a blend of methylating agent and toluene to make PX increases coke build-up and hence catalytic reaction system deactivation.

In one non-limiting embodiment of the invention, the catalyst activity decrease is less than 0.5% toluene and/or benzene conversion per day, preferably less than 0.1%.

In carrying out the process, the feed mixtures can be co-fed into a reactor containing one of the above mentioned catalytic reaction systems. The catalytic reaction system and reactants can be heated to reaction temperatures separately or together. Reaction can be carried out at a temperature from about 100–700° C., preferably from about 200–600° C.; at a pressure from about 1–300 atm ($1.01 \times 10^5$–$3.04 \times 10^7$ Pa), preferably from about 1–200 atm ($1.01 \times 10^5$–$2.03 \times 10^7$ Pa); and at a flow rate from about 0.01–100 $h^{-1}$ LHSV, preferably from about 1–50 $h^{-1}$ LHSV on a liquid feed basis. The composition of the feed, i.e. the mole ratio of $H_2/CO$ (and/or $CO_2$)/aromatic can be from of about 0.01–10/0.01–10/0.01–10, preferably from about 0.1–10/0.1–10/0.1–10.

As noted, typical methylating agents include or are formed from, but are not necessarily limited to hydrogen together with carbon monoxide and/or carbon dioxide, and/or methanol, but also dimethylether, methylchloride, methylbromide, and dimethylsulfide.

It is conceivable that in the scenarios described above, the toluene can be pure, or in a mixture with benzene. The benzene may alkylate to toluene, and/or ultimately to PX, with or without recycle. The presence of benzene may also enhance heat and/or selectivity control.

The method of this invention is expected to tolerate many different kinds of feed. Unextracted toluene, which is a mixture of toluene and similar boiling range olefins and paraffins, is preferred in one embodiment. For example, premium extracted toluene, essentially pure toluene, and extracted aromatics, essentially a relatively pure mixture of toluene and benzene, may also be used. Unextracted toluene and benzene which contains toluene, benzene, and olefins and paraffins that boil in a similar range to that of toluene or benzene, may also be employed. When unextracted feedstocks are used, it is important to crack the paraffins and olefins into lighter products that can be easily distilled. For example, the feed may contain one or more paraffins and/or olefins having at least 4 carbon atoms; the catalytic reaction systems have the dual function to crack the paraffins and/or olefins and methylate benzene or toluene to selectively produce PX.

Indeed, some of the catalytic reaction systems of this invention may be multifunctional in some embodiments, catalyzing a reaction or reactions of CO, $H_2$, and/or $CO_2$ and/or methanol to produce a methylating agent, catalyzing the selective methylation of toluene and/or benzene to produce PX, and catalyzing the cracking of paraffins and olefins into relatively lighter products.

The method of this invention is capable of producing mixtures of xylenes where PX comprises at least 30 wt. % of the mixture, preferably at least 36 wt. %, and most preferably at least 48 wt. %. The method of this invention is also capable of converting at least 5 wt. % of the aromatic compound to a mixture of xylenes, preferably greater than 15 wt. %.

Para-Xylene may be recovered from the process stream, for example by crystallization, for use in products such as terephthalic acid, dimethyl terephthalate, polyethylene terephthalate polymer, and the like, which in turn can be used to make synthetic fibers. There are three commercial techniques to recover PX, fractionation, adsorption (PAREX zeolite), and crystallization. In a preferred embodiment of the invention, combinations of these recovery techniques may used to lower capital costs. In another preferred embodiment of the invention, crystallization is used, particularly single-stage crystallization. Single-stage crystallization simply means that only one crystallization step is used on the product from the inventive process, which would be a simple and relatively inexpensive procedure. Because of the high quality product produced by the inventive process, it is expected that the PX proportion in the product from the inventive process may be 80% or more, while after one crystallization step, the proportion may be 99% or higher.

The selective methylation process of this invention has been discovered to have significant advantages when the possibility of using low cost, fuel-purpose syngas from gasifiers in a once-through (for the syngas feed) methylation reactor. In one non-limiting embodiment of the invention, the term fuel syngas is defined herein to include mixtures of CO and $H_2$, but may also contain compounds including, but not limited to, methane, methanol, di-methylether, $CO_2$, water, formaldehyde, ammonia, sulfur compounds such as $H_2S$, and mixtures thereof.

The proposed process arrangement 10 is shown in the FIGURE. At least part of a stream of fuel syngas 12 from a gasifier 14 (for e.g. turbines 16, furnaces, etc.) is diverted in stream 18 to be used in the process. Optionally, the stream may be fed via line 18 to a FLEXSORB® PS unit 20 or other conventional unit to remove sulfur therefrom. The optionally treated syngas 22 is mixed with reformate toluene heart cut 24 (in one non-limiting example) prior to entering the selective methylation reactor 26. Using A7/A8 fractionation column 28, xylenes 30 (which contain from about 85–90% PX) in the liquid product 29 are fractionated from the unreacted toluene, benzene and non-aromatic materials 32 which are recycled. An A8/A9 fractionation column (not shown) may be used, if necessary. The gas product 34, from gas/liquid separator 36, including unreacted syngas and cracked non-aromatics (NA), will be sent back to fuel (hence the term "once-through"). Due to the cracking of NA into light saturates, it is expected that more fuel gas would be returned than is consumed. Liquid product 30 is further purified in a crystallizer or existing PAREX unit 40 to give final product stream 42 of about 99.8% PX or higher and raffinate stream 44.

As noted, the process of the invention using fuel syngas has advantages including, but not limited to, (1) enabling the use of low-cost fuel syngas; (2) eliminating the need for recycling unreacted syngas and associated equipment; (3) eliminating the need for a significant purge stream of unreacted syngas; (4) enabling the use of the relatively low-cost unextracted toluene/benzene or straight reformate heart cut, and (5) eliminating the need for a significant purge stream of unreacted toluene, benzene and/or reformate.

The following examples will serve to illustrate the processes and merits of the present invention. It is to be understood that these examples are merely illustrative in nature and that the present process is not necessarily limited thereto.

EXAMPLE I

This example illustrates one of the methods in preparing a catalytic reaction system. The catalytic reaction system comprises (1) Cr and Zn mixed metal oxides; and (2) H-ZSM-5 zeolite with a $SiO_2/AlO_2$ molar ratio of 30(obtained from PQ Corporation, Valley Forge, Pa.). The Cr and Zn mixed metal oxides were prepared by co-precipitation of $Cr(NO_3)_3$ and $Zn(NO_3)_2$ with $NH_4OH$. 7.22 grams of $Cr(NO_3)_3$ and 13.41 grams of $Zn(NO_3)_2$ were dissolved in 100 ml distilled water separately. The two solutions were then mixed together. $NH_4OH$ was slowly added into the mixed solution with stirring until the pH value of the solution reached about 8. The precipitate was filtered and recovered. This precipitate was dried at a temperature of 120° C. for 12 hours, and then calcined in air at 500° C. for 6 hours. These Cr/Zn mixed metal oxides were ground into powders.

The catalytic reaction system was prepared by physically mixing powders of a composition of 50% (w/w) Cr/Zn mixed metal oxides and 50% (w/w) H-ZSM-5 zeolite. Powders of 2.0 grams of Cr/Zn mixed metal oxides and 2.0 grams of H-ZSM-5 zeolite were mixed thoroughly in a grinding mortar. The mixed catalytic reaction system powders were pelletized and screened to 8–12 mesh (0.27–0.17 cm) particles.

EXAMPLE II

This example shows that the synthesis of xylenes with syngas alkylation of toluene can be achieved in a catalytic process as disclosed by prior art. However, this example indicates that such a process cannot achieve high para-xylene selectivity when the aluminosilicate component in the catalytic reaction system is not modified for shape selectivity. The catalytic reaction system was prepared as in Example I. The catalytic reaction system was reduced at 350° C. under 5% $H_2$ (balanced with 95% $N_2$) for 16 hours at 1 atm prior to reaction.

The catalytic reaction system was evaluated with co-feed of syngas (CO and $H_2$) and toluene with a composition of $H_2/CO$/toluene of 2/1/0.5 (molar ratio), a temperature of about 450° C., and a pressure of about 18 atm (i.e., 250 psig, $1.82 \times 10^6$ Pa); The WHSV (Weight Hourly Space Velocity) was about 3 $h^{-1}$ for toluene with respect to the catalytic reaction system. Test results are given in Table 1. Similar to prior art reported, the selectivity of para-xylene in xylenes is about 25%, which is close to equilibrium, with toluene conversion of 28.6% and xylene selectivity of 71.1%.

TABLE 1

| Synthesis of PX using Zeolite not Selectivated | | | | |
|---|---|---|---|---|
| CO conv. % | $H_2$ conv. % | Toluene conv. % | Xylene select. % | PX select. % |
| 31.7 | 17.1 | 28.6 | 71.1 | 25.0 |

EXAMPLE III

This example illustrates the poor product quality derived from a conventional metal oxides/aluminosilicate system. The catalytic reaction system was a physical mixture of 50 wt % of ZSM-5 in the form of powder (CBV8020, an aluminosilicate zeolite obtained from PQ Corp., Valley Forge, Pa.) and 50 wt % of a composite of oxides of copper, zinc, and aluminum also in the form of powder, (C-79, obtained from UCI Inc., Louisville, Ky.). The two components were mixed thoroughly, pelletized, and screened to 8/12 (0.27–0.17 cm) mesh particles. The catalytic reaction system particles were packed in a stainless steel reactor and reduced with a gas mixture of 2% hydrogen in 98% nitrogen at 250 C and 1 atm ($1.01 \times 10^5$ Pa) for 16 hours. The feed stream was a mixture of syngas and toluene having a molar ratio of 1:1:0.47 (hydrogen:carbon monoxide:toluene). The reaction conditions were set at 350° C. and 350 psig ($2.53 \times 10^6$ Pa). A distribution of the liquid hydrocarbon products is given in Table 2. It is seen that the catalytic reaction system made 39.80% of undesirable heavy aromatic compounds (A9, A10, & A11+). The lack of para-selectivity was indicated by the near equilibrium concentration (24.14%) of PX in the xylene-fraction products.

TABLE 2

Conventional Metal Oxides/Aluminosilicate System

| Products | wt % | $A_8$-Fraction. wt % |
|---|---|---|
| Non-aromatics | 1.54 | |
| Benzene | 1.07 | |
| Ethylbenzene | 0.40 | 0.69 |
| para-Xylene | 13.90 | 24.14 |
| meta-Xylene | 30.36 | 52.72 |
| ortho-Xylene | 12.93 | 22.45 |
| A9–A10 | 27.66 | |
| A11+ | 12.14 | |

EXAMPLE IV

This example illustrates the superior performance of the proposed metal oxides/silicon-aluminophosphate system of this invention. The catalytic reaction system was a physical mixture of 50 wt % of SAPO-11 material in the form of powder (an aluminophosphate material obtained from UOP) and 50 wt % of the same C-79 composite as in Example III. The two components were mixed thoroughly, pelletized, and screened to 8/12 mesh (0.27–0.17 cm) particles. The catalytic reaction system particles were packed in a stainless steel reactor and reduced with a gas mixture of 2% hydrogen in 98% nitrogen at 250° C. and 1 atm ($1.01 \times 10^5$ Pa) for 16 hours. The feed stream was a mixture of syngas and toluene having a molar ratio of 1:1:0.45 (hydrogen:carbon monoxide:toluene). The reaction conditions were set at 350° C. and 350 psig ($2.53 \times 10^6$ Pa). A distribution of the liquid hydrocarbon products is given in Table 3. It is seen that the catalytic reaction system made much less undesirable heavy aromatic compounds (11.29% for A9, A10, & A11+). The improvement in para-selectivity was indicated by the much-higher-than-equilibrium concentration (45.52%) of PX in the xylene-fraction products.

TABLE 3

Metal Oxides/Silicon-Aluminophosphate System of the Invention

| Products | wt % | $A_8$-Fraction. wt % |
|---|---|---|
| Non-aromatics | 21.11 | |
| Benzene | 1.25 | |
| Ethylbenzene | 1.09 | 1.64 |
| para-Xylene | 30.20 | 45.52 |
| meta-Xylene | 21.81 | 32.87 |
| ortho-Xylene | 13.25 | 19.97 |
| A9–A10 | 9.47 | |
| A11+ | 1.82 | |

EXAMPLE V

This example illustrates the preparation of para-alkyl selectivated ZSM-5 zeolite with magnesium oxide as the selectivating agent. 11.68 grams of magnesium hydroxide was mixed with distilled water. To the solution was added 20.44 grams of ammonium nitrate and 33.54 grams of phthalic acid in sequence. The mixture was heated to obtain a clear solution, which was cooled to room temperature before use. 14.80 grams of the solution was mixed with 7.77 grams of a ZSM-5 zeolite ($SiO_2/AlO_2$ of 50). The mixture was heated to evaporate the water solvent. The remaining solid was dried at 120° C. for 12 hours and calcined at 500° C. for 8 hours with air purge. The para-alkyl selectivated ZSM-5 zeolite contained approximately 9 wt. % of magnesium oxide.

EXAMPLE VI

This example illustrates the preparation of another type of the catalytic reaction system. The catalytic reaction system comprises (1) Mn and Zn mixed metal oxides, and (2) MgO modified H-ZSM-5 zeolite with a $SiO_2/AlO_2$ of 38. The same preparation procedures as that given in Example V were used. The Mn and Zn mixed metal oxides were prepared by co-precipitation of $Mn(NO_3)_2$ and $Zn(NO_3)_2$ with $NH_4OH$. 4.14 grams of $Mn(NO_3)_2$ and 13.44 grams of $Zn(NO_3)_2$ were dissolved in 100 ml distilled water separately. The two solutions were then mixed together. $NH_4OH$ was slowly added into the mixed solution with stirring until the pH value of the solution reached about 7.5. The precipitate was filtered and recovered. This precipitate was dried at a temperature of 120° C. for 12 hours, and then calcined in air at 500° C. for 6 hours. These Mn/Zn mixed metal oxides were ground into powders.

The catalytic reaction system was prepared by physically mixing powders of a composition of 50% (w/w) Mn/Zn mixed metal oxides and 50% (w/w) MgO modified H-ZSM-5 zeolite. Powders of 2.0 grams of Mn/Zn mixed metal oxides and 2.0 grams of MgO modified H-ZSM-5 zeolite were mixed thoroughly in a grinding mortar. The mixed catalytic reaction system powders were pelletized and screened to 8–12 mesh (0.27–0.17 cm) particles.

EXAMPLE VII

This example illustrates that metal oxides other than Cr/Zn mixed metal oxides are also suitable as one of the components in the catalytic reaction system used in the xylenes synthesis with syngas alkylation of toluene. In addition, this example demonstrates that high para-xylene selectivity can be obtained when the aluminosilicate component in the catalytic reaction system is modified for shape selectivity. The catalytic reaction system was prepared as in Example VI. The catalytic reaction system was reduced at 350° C. under 5% $H_2$ (balanced with 95% $N_2$) for 16 hours at 1 atm prior to reaction.

The reaction was conducted under similar conditions to those in Example II. Test results are given in Table 4. The para-xylene selectivity in xylenes is about 76.0% with toluene conversion of 10.9% and xylene selectivity of 85.4%. Compared to Example II, the para-xylene selectivity is significantly enhanced when the aluminosilicate component is modified for shape selectivity.

TABLE 4

Synthesis of PX using Zeolite Modified for Shape Selectivity

| CO conv. % | $H_2$ conv. % | Toluene Conv. % | Xylene select. % | PX select. % |
|---|---|---|---|---|
| 11.7 | 5.6 | 10.9 | 85.4 | 76.0 |

EXAMPLE VIII

This example illustrates that the toluene conversion can be increased with a similar high para-xylene selectivity when the reaction operation conditions are optimized. The catalytic reaction system used in this example was comprised of a composition of (1) 50% (w/w) Cr, Zn, and Mg mixed metal oxides, and (2) 50% (w/w) MgO modified H-ZSM-5 zeolite with a $SiO_2/AlO_2$ of 38. The Cr, Zn, and Mg mixed metal oxides were prepared in a similar method as described in Example I with co-precipitation of $Cr(NO_3)_3$, $Zn(NO_3)_2$, and $Mg(NO_3)_2$ with $NH_4OH$. The magnesium oxide-modified ZSM zeolite was prepared as described in Example V. The catalytic reaction system was prepared by physical mixing as described in Example I. The catalytic reaction system was reduced at 350° C. under 5% $H_2$ (balanced with 95% $N_2$) for 16 hours at 1 atm ($1.01 \times 10^5$ Pa) prior to reaction.

The catalytic reaction system was evaluated with co-feed of syngas (CO and $H_2$) and toluene with a varied composition of $H_2$/CO/toluene, a temperature from 450–490° C., and a pressure in the range of 18–28 atm (i.e. 250–390 psig, $1.82 \times 10^6$–$2.83 \times 10^6$ Pa). The WHSV (Weight Hourly Space Velocity) varied from 1.5–6 $h^{-1}$ for toluene with respect to the catalytic reaction system. Some of the test results are shown in Table 5. As shown in Table 5, a toluene conversion of 34% was achieved with a similar para-xylene selectivity when the reaction was operated at a temperature of ca. 460° C., a pressure of ca. 28 atm (390 psig; $2.83 \times 10^5$ Pa), and a WHSV of ca. 1.5 $h^{-1}$ for toluene with respect to catalytic reaction system.

TABLE 5

Synthesis of PX using Zeolite Modified for Shape Selectivity

| | | | | |
|---|---|---|---|---|
| Reaction Temperature, ° C. | 460 | 469 | 460 | 475 |
| Reaction Pressure, psig | 250 | 390 | 250 | 250 |
| Reaction Pressure, Pa | $1.82 \times 10^6$ | $2.83 \times 10^6$ | $1.82 \times 10^6$ | $1.82 \times 10^6$ |
| Feed Composition, mole ratio | 2/1/0.25 | 2/1/0.25 | 2/1/0.5 | 2/1/0.5 |
| WHSV, $h^{-1}$ (Tol./Catalyst) | 1.5 | 1.5 | 3 | 3 |
| CO conv. % | 18.4 | 29.2 | 17.4 | 18.1 |
| $H_2$ conv. % | 6.6 | 9.4 | 7.4 | 7.6 |
| Toluene conv. % | 26.0 | 34.7 | 13.6 | 15.5 |
| Xylene select. % | 84.2 | 80.1 | 82.4 | 86.3 |
| PX select. % | 74.5 | 75.2 | 88.0 | 85.1 |

EXAMPLE IX

This example illustrates the problems of low methanol selectivity and fast catalytic reaction system deactivation associated with a low aromatic/methanol ratio and one-time methanol injection. The catalytic reaction system was extrudates of SAPO-11 material obtained from UOP. The extrudates were ground and screened to 8–12 mesh (0.27–0.17 cm) and calcined at 550° C. under air for 16 hours prior to use. The catalytic reaction system was evaluated at 350° C., 25 atm (350 psig, $2.53 \times 10^6$ Pa), and 8 $h^{-1}$ WHSV. The feed was a mixture of toluene/methanol with a molar ratio of 3.6. Test results are given in Table 6. It is seen that the methanol selectivity decreased from 70.0% to 55.0% over a test period of 24 hours. Furthermore, the system was experiencing a severe catalytic reaction system deactivation as indicated by the decreasing toluene conversion from 18.5% to 15.1%.

TABLE 6

Synthesis of PX with Low Methanol Selectivity and Catalytic Reaction System Deactivation

| | | |
|---|---|---|
| Toluene/Methanol (mole) | | 3.6 |
| Hours on Stream | 2 | 24 |
| Toluene Total Conversion | 18.5% | 15.1% |
| Toluene Conversion due to Disproportionation | 0% | 0% |

TABLE 6-continued

Synthesis of PX with Low Methanol Selectivity and Catalytic Reaction System Deactivation

| | | |
|---|---|---|
| Toluene/Methanol (mole) | | 3.6 |
| Toluene Conversion due to Methylation | 18.5% | 15.1% |
| Methanol Total Conversion | 100% | 97.0% |
| Methanol consumed by mono- and multiple methylation of toluene | 70.0% | 55.0% |
| Methanol consumed by other Reactions | 30.0% | 42.0% |

EXAMPLE X

This example demonstrates the problems of fast catalytic reaction system deactivation for MgO para-alkyl selectivated H-ZSM-5 in toluene methylation with low toluene/methanol ratio and one-time methanol injection. The catalytic reaction system was MgO-para-alkyl selectivated H-ZSM-5 with a $SiO_2/AlO_2$ ratio of 38. The same preparation procedure as that given in Example V was used. The catalytic reaction system was pelletized and screened to 40–60 mesh (0.042–0.025 cm). The catalytic reaction system was tested at 460° C., 1 atm, and 14 $h^{-1}$ WHSV. The feed was a mixture of toluene/methanol with a molar ratio of 1.0. The results presented in Table 7 indicate that although MgO para-alkyl selectivation of H-ZSM-5 improves the para-xylene selectivity, this catalytic reaction system still exhibits serious catalytic reaction system deactivation as indicated by the decreasing toluene conversion from 20.5% to 8.5%.

TABLE 7

Synthesis of PX Showing Catalytic Reaction System Deactivation

| | | | | |
|---|---|---|---|---|
| Toluene/Methanol (molar ratio) | | 1/1 | | |
| Hours on Stream | 0.5 | 2 | 2 | 2.5 |
| Toluene Conversion, % | 19.3 | 19.8 | 20.5 | 8.5 |
| Methanol Conversion, % | 100 | 100 | 100 | 99.6 |
| Xylene Selectivity, % | 76.7 | 76.4 | 54.1 | 86.1 |
| Para-Xylene Selectivity, % | 83.3 | 83.3 | 86.5 | 76.3 |

EXAMPLE XI

This example demonstrates that the catalytic reaction system would suffer from deactivation for syngas methylation of toluene if the aluminosilicate component in the catalytic reaction system is not properly para-alkyl selectivated. The test was conducted in the same manner as Example II. The reaction was monitored as time-on-stream, and the results are shown in Table 8. The catalytic reaction system displays some deactivation over a period of 18 hours as indicated by the decreasing toluene conversion from 35.3% to 28.6%.

TABLE 8

Synthesis of PX Showing Catalytic Reaction System Deactivation

| | | | |
|---|---|---|---|
| CO/Toluene (molar ratio) | | 2/1/0.5 | |
| Hours on Stream | 2 | 9.5 | 18.2 |
| Toluene Conversion, % | 35.3 | 31.1 | 28.6 |
| CO Conversion, % | 33.6 | 31.4 | 31.7 |
| $H_2$ Conversion, % | 17.8 | 16.4 | 17.1 |
| Xylene Selectivity, % | 67.4 | 69.8 | 71.1 |
| Para-Xylene Selectivity, % | 24.8 | 24.9 | 25.0 |

EXAMPLE XII

This example illustrates that the process disclosed in this invention has a much higher activity maintenance for PX synthesis than the conventional methanol-toluene methylation process.

The catalytic reaction system used in this example comprised (1) Cr and Zn mixed metal oxides, and (2) MgO modified H-ZSM-5 zeolite with a $SiO_2/AlO_2$ of 38. The Cr and Zn mixed metal oxides were prepared as described in Example I. The magnesium oxide-modified ZSM zeolite was prepared as described in Example V. The Cr/Zn mixed metal oxides were ground into powders. The catalytic reaction system was prepared by physically mixing powders of a composition of (1) 34% (w/w) Cr and Zn mixed metal oxides, and (2) 66% MgO modified H-ZSM-5 zeolite. The mixed catalytic reaction system powders were pelletized and screened to 8–12 mesh (0.27–0.17 cm) particles. The catalytic reaction system was reduced at 350° C. under 5% $H_2$ (balanced with 95% $N_2$) for 16 hours at 1 atm ($1.01 \times 10^5$ Pa) prior to reaction. The organometallic modifier was magnesium phthalate.

The catalytic reaction system was evaluated with similar operation conditions as those in Example II. Test results are given in Table 9. It is seen that the catalytic reaction system had a stable activity for toluene conversi on with stable PX selectivity.

TABLE 9

Higher Activity Maintenance for Para-Xylene Synthesis

| $H_2$/CO/Toluene (molar ratio) | 2/1/0.5 | | | |
|---|---|---|---|---|
| Hours on Stream, h | 5.5 | 24 | 91.5 | 120 |
| Toluene Conversion, % | 17.0 | 18.0 | 17.4 | 17.1 |
| CO Conversion, % | 20.5 | 20.7 | 17.9 | 17.8 |
| $H_2$ Conversion, % | 8.5 | 9.3 | 9.1 | 9.1 |
| Xylene Selectivity, % | 76.5 | 80.2 | 80.6 | 80.5 |
| Para-Xylene Selectivity, % | 63.4 | 67.0 | 71.4 | 75.2 |

EXAMPLE XIII

This example illustrates the feasibility of using unextracted toluene as feed for syngas alkylation of toluene with the catalytic reaction system disclosed in this invention. The catalytic reaction system used in this example comprised (1) mixed Cr and Zn oxides, and (2) a MgO modified H-ZSM-5 zeolite prepared using the methods described in Example V. The Cr and Zn mixed metal oxides were prepared as described in Example I. These Cr/Zn mixed metal oxides were ground into powders. The catalytic reaction system was prepared by physically mixing powders of a composition of (1) 50% (w/w) mixed Cr and Zn oxides, and (2) 50% MgO modified H-ZSM-5 zeolite. The mixed catalytic reaction system powders were pelletized and screened to 8–12 mesh particles. The catalytic reaction system was reduced at 350° C. under 5% $H_2$ (balanced with 95% $N_2$) for 16 hours at 1 atm prior to reaction.

The catalytic reaction system was tested first with a co-feed of syngas and toluene, and then with a co-feed of syngas and a toluene/heptane mixture at weight percent of 70%/30%. The reaction was conducted at a temperature of about 460° C. and a pressure of about 21.5 atm (i.e., 300 psig; $2.17 \times 10^6$ Pa). The WHSV was about 1.5 $h^{-1}$ for toluene and toluene/heptane mixture with respect to the catalytic reaction system. The results presented in Table 10 indicate that the catalytic reaction system is able to carry out heptane cracking reaction and toluene methylation reaction simultaneously. The system demonstrated a good activity maintenance for both reactions. This feature implies that the catalytic reaction system could be used to process unextracted toluene.

TABLE 10

Simultaneous Selectivity to PX and Heptane Cracking Showing Catalytic reaction system Stability

| Feed | $H_2$/CO/Toluene | | $H_2$/CO/Toluene + Heptane | |
|---|---|---|---|---|
| Composition (molar ratio) | 2/1/0.25 | 2/1/0.25 | 2/1/0.25 | 2/1/0.25 |
| Hours on Stream | 18 | 73 | 89 | 118 |
| Toluene Conversion, % | 27.4 | 26.8 | 32.7 | 34.2 |
| Heptane Conversion, % | — | — | 65.7 | 65.0 |
| CO Conversion, % | 34.1 | 35.0 | 38.4 | 38.3 |
| $H_2$ Conversion, % | 10.6 | 14.9 | 20.7 | 13.6 |
| Xylene Selectivity, % | 85.6 | 83.7 | 55.5 | 55.2 |
| Para-Xylene Selectivity, % | 64.2 | 65.7 | 64.9 | 65.5 |

EXAMPLE XIV

In focusing on improving selectivity to PX and conversion of toluene and/or benzene and syngas, and the gasloil ratio, the following fuel syngas once-through performance has been demonstrated with a catalyst system of mixed oxide/selectivated zeolite.

450° C., 300–400 psig ($3.04 \times 10^7$–$4.05 \times 10^7$ Pa), syngas ($H_2$/CO=1/1) to reformate ratio=4:1–12:1.

Toluene conversion 20–30% (target: 25–35%), syngas conversion 20–30%.

PX selectivity 70–80% (target: 85–90+%), xylene selectivity 80–85% (target: 80+%).

65% of the NA in the reformate can be cracked to light saturates.

EXAMPLE XV

The once-through operation of the invention seems to fit well with gasifier fuel syngas. The objective of gasifiers is to upgrade heavy oil or wastes (e.g. deasphalter bottoms rock (DAR), steam cracking tar (S/C tar), etc.) to syngas at fuel value. Essentially, as envisioned in the present invention, the selective methylation reactor would just skim off a fraction (e.g. about 25%) of the syngas fuel to make PX. A rough calculation indicates that when comparing the heating value (HHV) of the syngas entering the process and the residual syngas/light saturates leaving, the fuel gas increases in mass flow by greater than 20%, and the heating value increases by greater than 50%, as shown in Table 11. As a result, the down stream equipment (e.g. turbines, furnaces, and the like) probably would not be significantly affected by the presence of the selective methylation reactor.

TABLE 11

Methylation Reactor Fuel Balance

| | Net Feed kgm/hr | Net Prod. kgm/hr | C in Comp. | H in Comp. | O in Comp | C in | C out | H2 in | H2 out | O2 in | O |
|---|---|---|---|---|---|---|---|---|---|---|---|
| CO | 2000 | 1329.6 | 1.0 | 0.0 | 1.0 | 2000.0 | 1329.6 | 0.0 | 0.0 | 2000.0 | |
| H2 | 2000 | 1470.7 | 0.0 | 2.0 | 0.0 | 0.0 | 0.0 | 4000.0 | 2941.5 | 0.0 | |
| CO2 | | 335.2 | 1.0 | 0.0 | 2.0 | 0.0 | 335.2 | 0.0 | 0.0 | 0.0 | |
| Benzene | 1.10 | 0.0 | 6.0 | 6.0 | 0.0 | 6.6 | 0.0 | 6.6 | 0.0 | 0.0 | |
| 24DM Pentane | 0.08 | 0.0 | 7.0 | 16.0 | 0.0 | 0.5 | 0.0 | 1.2 | 0.0 | 0.0 | |
| Cyclohexane | 0.02 | 0.0 | 6.0 | 12.0 | 0.0 | 0.1 | 0.0 | 0.3 | 0.0 | 0.0 | |
| 2M Hexane | 32.15 | 0.0 | 7.0 | 16.0 | 0.0 | 225.0 | 0.0 | 514.4 | 0.0 | 0.0 | |
| 33DM Pentane | 0.76 | 0.0 | 7.0 | 16.0 | 0.0 | 5.3 | 0.0 | 12.1 | 0.0 | 0.0 | |
| Cis 13DM Cyclopentane | 6.20 | 0.0 | 7.0 | 14.0 | 0.0 | 43.4 | 0.0 | 86.8 | 0.0 | 0.0 | |
| 3M Hexane | 56.58 | 0.0 | 7.0 | 16.0 | 0.0 | 396.1 | 0.0 | 905.3 | 0.0 | 0.0 | |
| Heptane | 31.94 | 0.0 | 7.0 | 16.0 | 0.0 | 223.6 | 0.0 | 511.1 | 0.0 | 0.0 | |
| Heptene | 4.40 | 0.0 | 7.0 | 14.0 | 0.0 | 30.8 | 0.0 | 61.6 | 0.0 | 0.0 | |
| Methyl cyclohexane | 2.20 | 0.0 | 7.0 | 14.0 | 0.0 | 15.4 | 0.0 | 30.8 | 0.0 | 0.0 | |
| 25DM Hexane | 6.60 | 0.0 | 8.0 | 18.0 | 0.0 | 52.8 | 0.0 | 118.9 | 0.0 | 0.0 | |
| Toluene | 333.0 | 0.0 | 7.0 | 8.0 | 0.0 | 2331.0 | 0.0 | 2664.0 | 0.0 | 0.0 | |
| 2M Heptane | 20.20 | 0.0 | 8.0 | 18.0 | 0.0 | 161.6 | 0.0 | 363.5 | 0.0 | 0.0 | |
| 244TM Pentene | 0.41 | 0.0 | 8.0 | 16.0 | 0.0 | 3.3 | 0.0 | 6.6 | 0.0 | 0.0 | |
| Ethyl Benzene | 1.13 | 0.0 | 8.0 | 10.0 | 0.0 | 9.0 | 0.0 | 11.3 | 0.0 | 0.0 | |
| ParaXylene | 0.61 | 294.6 | 8.0 | 10.0 | 0.0 | 4.9 | 2357.0 | 6.1 | 2946.3 | 0.0 | |
| MetaXylene | 1.30 | 31.4 | 8.0 | 10.0 | 0.0 | 10.4 | 251.0 | 13.0 | 313.7 | 0.0 | |
| Octane | 4.29 | 0.0 | 8.0 | 18.0 | 0.0 | 34.3 | 0.0 | 77.3 | 0.0 | 0.0 | |
| 3M Octane | 0.02 | 0.0 | 9.0 | 20.0 | 0.0 | 0.1 | 0.0 | 0.3 | 0.0 | 0.0 | |
| OrthoXylene | 0.13 | 10.2 | 8.0 | 10.0 | 0.0 | 1.0 | 81.2 | 1.3 | 101.5 | 0.0 | |
| Nonane | 0.00 | 0.0 | 9.0 | 20.0 | 0.0 | 0.0 | 0.0 | 0.0 | 0.0 | 0.0 | |
| Cracked Gas (50% C3H8 + 50% C4H10) | 0.00 | 343.3 | 3.5 | 9.0 | 0.0 | 0.0 | 1201.5 | 0.0 | 3089.5 | 0.0 | |
| TOTAL | 503.13 | 679.4 | | | | 5555.5 | 5555.5 | 9392.5 | 9392.5 | 2000.0 | |

In a preferred embodiment, the incoming gasifier syngas would have to be optionally treated with an amine-type cleanup, or other conventional process, to remove sulfur contaminants. A FLEXSORB® PS unit could be employed. In some cases, this unit would need to remove $CO_2$ as well as sulfur containing compounds such as $H_2S$ and COS. It would have to be studied whether sulfur remaining in the substantially desulfurized fuel syngas would adversely affect the catalyst used in the selective methylation reactor.

In the foregoing specification, the invention has been described with reference to specific embodiments thereof, and has been demonstrated as effective in providing methods for directly and selectively producing PX from benzene and/or toluene and hydrogen together with CO and/or $CO_2$ from fuel syngas using a catalytic reaction system. However, it will be evident that various modifications and changes can be made thereto without departing from the broader spirit or scope of the invention as set forth in the appended claims. Accordingly, the specification is to be regarded in an illustrative rather than a restrictive sense. For example, specific combinations of catalyst components, other than those specifically tried, in other proportions or ratios or mixed in different ways, falling within the claimed parameters, but not specifically identified or tried in a particular method to improve the PX selectivity herein, are anticipated to be within the scope of this invention. Further, various combinations of reactants, catalytic reaction systems, catalyst modifiers, and control techniques not explicitly described but nonetheless falling within the appended claims are understood to be included.

What is claimed is:

1. A method for forming para-xylene (PX) from fuel syngas comprising reacting the fuel syngas comprising methane and water on a once-through basis with a feed including an aromatic compound selected from the group consisting of toluene, benzene and mixtures thereof, in the presence of a catalytic reaction system which converts greater than 15 wt. % of the aromatic compound to a mixture of xylenes, where PX comprises at least 48 wt. % of the mixture of xylenes, and where the catalytic reaction system comprises:

a first component selected from the group consisting of metals and metal oxides, where the metal element is selected from the group consisting of the Groups 1, 2, 3, 4, 5, 6, 7, 8, 9, 10, 11, 12, 13, 14, 15, and 16 of the Periodic Table of Elements (new IUPAC notation); and a second component selected from the group consisting of crystalline or amorphous aluminosilicates having one-dimensional channel structure, para-alkyl selectivated amorphous aluminosilicates, para-alkyl selectivated substituted aluminosilicates, crystalline or amorphous substituted silicates having one-dimensional channel structure, para-alkyl selectivated substituted silicates, crystalline or amorphous aluminophosphates, crystalline or amorphous substituted aluminophosphates, para-alkyl selectivated crystalline or amorphous aluminophosphates, para-alkyl selectivated zeolite-bound zeolite, para-alkyl selectivated substituted aluminophosphates, and mixtures thereof.

2. The method of claim 1 further comprising:
methylating benzene to toluene, and
methylating toluene to PX.

3. The method of claim 1 where the first components and the second components are combined in a manner selected from the group consisting of chemically mixed using solutions, physically mixed, stacked, and combinations thereof.

4. The method of claim 1 where the para-selectivated second component of the catalytic reaction system is formed by para-alkyl selectivation comprising modification with an agent selected from the group consisting of compounds of elements selected from Groups 1 through 16, and mixtures thereof.

5. The method of claim 4 where the compound is an organometallic salt comprising:
   an organic anion having functional groups selected from the group consisting of carboxylic groups, phenolic groups and mixtures thereof; and
   a metal cation selected from the group consisting of the element(s) of Groups 1, 2, 3, 4, 5, 6, 7, 8, 9, 10, 11, 12, 13, 14, 15, and 16 (new IUPAC notation).

6. The method of claim 1 where the para-selectivated second component of the catalytic reaction system is formed by para-alkyl selectivation comprising modification with an agent selected from the group consisting of organometallic compounds, carbon compounds, silicon compounds, phosphorus compounds, boron compounds, antimony compounds, magnesium compounds, and mixtures thereof.

7. The method of claim 1 where the para-alkyl selectivated substituted silicates are selected from the group consisting of gallosilicates, borosilicates and ferrosilicates.

8. The method of claim 1 further comprising recovering PX by first removing unreacted syngas and at least a portion of any saturated compounds.

9. The method of claim 8 wherein the PX is further recovered by a process selected from the group consisting of fractionation, crystallization, adsorption, and combinations thereof.

10. The method of claim 1 where the catalytic reaction system functions to catalyze at least one reaction in addition to forming PX.

11. The method of claim 10 where the feed further comprises at least one compound selected from the group consisting of paraffins and olefins having at least 4 carbon atoms and where the catalytic reaction system cracks the paraffin or olefin.

12. The method of claim 1 where the catalytic reaction system activity decrease is less than 0.5% toluene and/or benzene conversion per day.

13. The method of claim 1 where the conversion of aromatic compound to a mixture of xylenes is greater than 15%.

14. The method of claim 1 where the fuel syngas is desulfurized prior to reacting it with the feed.

15. The method of claim 1 where the feed is selected from the group consisting of unextracted benzene, unextracted toluene, straight reformate benzene heart cut, straight reformate toluene heart cut, extracted benzene, extracted toluene, and mixtures thereof.

16. A method for forming para-xylene (PX) from fuel syngas comprising:
   providing a catalytic reaction system comprising
      a first component selected from the group consisting of metals and metal oxides, where the metal element is selected from the group consisting of the Groups 1, 2, 3, 4, 5, 6, 7, 8, 9, 10, 11, 12, 13, 14, 15, and 16 of the Periodic Table of Elements; and
      a second component selected from the group consisting of crystalline or amorphous aluminosilicates having one-dimensional channel structure, para-alkyl selectivated amorphous aluminosilicates, para-alkyl selectivated substituted aluminosilicates, crystalline or amorphous substituted silicates having one-dimensional channel structure, para-alkyl selectivated substituted silicates, crystalline or amorphous aluminophosphates, crystalline or amorphous substituted aluminophosphates, para-alkyl selectivated crystalline or amorphous aluminophosphates, para-alkyl selectivated zeolite-bound zeolite, para-alkyl selectivated substituted aluminophosphates, and mixtures thereof;
   reacting the fuel syngas comprising methane and water on a once-through basis with an aromatic compound selected from the group consisting of toluene, benzene and mixtures thereof with a methylating agent formed from the fuel syngas, in the presence of the catalytic reaction system to produce a xylene fraction having a PX concentration; and
   recovering PX where greater than 15% of the aromatic compound is converted to a xylene fraction and where the PX concentration recovered in the xylene fraction is greater than 48 wt. %.

17. The method of claim 16 where the first components and the second components are combined in manner selected from the group consisting of chemically mixed using solutions, physically mixed, stacked, and combinations thereof.

18. The method of claim 16 where the para-selectivated second component of the catalytic reaction system is formed by para-alkyl selectivation comprising modification with an agent selected from the group consisting of compounds of elements selected from Groups 1 through 16, and mixtures thereof.

19. The method of claim 18 where the compound is an organometallic salt comprising:
   an organic anion having functional groups selected from the group consisting of carboxylic groups, phenolic groups and mixtures thereof; and
   a metal cation selected from the group consisting of the element(s) of Groups 1, 2, 3, 4, 5, 6, 7, 8, 9, 10, 11, 12, 13, 14, 15, and 16 (new IUPAC notation).

20. The method of claim 16 where the para-selectivated second component of the catalytic reaction system is formed by para-alkyl selectivation comprising modification with an agent selected from the group consisting of organometallic compounds, carbon compounds, silicon compounds, phosphorus compounds, boron compounds, antimony compounds, magnesium compounds, and mixtures thereof.

21. The method of claim 16 further comprising
   recovering PX by first removing unreacted syngas and at least a portion of any saturated compounds, and
   further recovering PX by a process selected from the group consisting of fractionation, crystallization, adsorption, and combinations thereof.

22. The method of claim 16 where the catalytic reaction system functions to catalyze at least one reaction in addition to forming PX, where the feed further comprises at least one paraffin having at least 7 carbon atoms and where the catalytic reaction system cracks the paraffin.

23. The method of claim 16 where the catalytic reaction system activity decrease is less than 0.5% toluene and/or benzene conversion per day.

24. The method of claim 16 in the absence of unused fuel syngas recycle back to the catalytic methylation reaction.

25. The method of claim 16 where the feed is selected from the group consisting of unextracted benzene, unextracted toluene, straight reformate benzene heart cut, straight reformate toluene heart cut, extracted benzene, extracted toluene, and mixtures thereof.

26. The method of claim 16 where the fuel syngas is desulfurized prior to reacting it with the feed.

* * * * *